(12) United States Patent
Sorensen et al.

(10) Patent No.: US 8,805,619 B2
(45) Date of Patent: Aug. 12, 2014

(54) TISSUE DISORDER IMAGING ANALYSIS

(75) Inventors: Gregory Sorensen, Lexington, MA (US); Nina M. Menezes, Boston, MA (US); Hakan Ay, Charlestown, MA (US)

(73) Assignee: The General Hospital Corporation, Boston, MA (US)

( * ) Notice: Subject to any disclaimer, the term of this patent is extended or adjusted under 35 U.S.C. 154(b) by 1872 days.

(21) Appl. No.: 10/532,885

(22) PCT Filed: Oct. 28, 2003

(86) PCT No.: PCT/US03/34308
§ 371 (c)(1),
(2), (4) Date: Mar. 3, 2006

(87) PCT Pub. No.: WO2004/040437
PCT Pub. Date: May 13, 2004

(65) Prior Publication Data
US 2006/0142983 A1    Jun. 29, 2006

Related U.S. Application Data

(60) Provisional application No. 60/421,736, filed on Oct. 28, 2002.

(51) Int. Cl.
*G01N 33/50* (2006.01)
(52) U.S. Cl.
USPC .......................................................... 702/19
(58) Field of Classification Search
None
See application file for complete search history.

(56) References Cited

U.S. PATENT DOCUMENTS

| | | | |
|---|---|---|---|
| 6,430,430 B1 | 8/2002 | Gosche | |
| 6,463,315 B1 | 10/2002 | Klingberg | |
| 7,020,578 B2 * | 3/2006 | Sorensen et al. | 702/181 |
| 2002/0103429 A1 * | 8/2002 | deCharms | 600/410 |

FOREIGN PATENT DOCUMENTS

WO    WO 01/56466 A2    8/2001

* cited by examiner

*Primary Examiner* — Jason Sims
(74) *Attorney, Agent, or Firm* — Quarles & Brady, LLP

(57) ABSTRACT

Methods and systems are described for quantitatively determining a score for a patient having a disorder, e.g., a stroke, in a tissue, such as the brain, by analyzing both the extent and location of damage to the tissue caused by the disorder.

17 Claims, 11 Drawing Sheets

"Risk/Reward" Map

Hazard Atlas

Risk Map

Combining Risk Map and Hazard Map to Highlight Possible Salvageability

TISSUE DISORDER IMAGING ANALYSIS

CROSS-REFERENCE TO RELATED APPLICATIONS

This application claims priority from PCT Application No. PCT/US03/034308 filed on Oct. 28, 2003, which claims the benefit of U.S. Provisional Application No. 60/421,736 filed on Oct. 28, 2002, both of which are incorporated by reference.

TECHNICAL FIELD

The invention relates to methods of evaluating disorders in tissue, such as the severity of a stroke or other disorder in the brain.

BACKGROUND

Quantitative imaging tools such as computer tomography (CT) and magnetic resonance imaging (MRI) are used to image various tissues such as the brain heart, and joints. For example, in the brain, various disorders such as stroke, autism, Alzheimer Disease, Multiple Sclerosis, and schizophrenia, can be imaged using these and other known techniques. Such images often display the regions that are at risk or are damaged, e.g., with a structural or functional lesion, caused by the disease or disorder, or by physical or neurological trauma. Many of these other diseases, such as stroke, have clinical rating scales that are numerical and correlate physical behavior and degree of recovery with physical or functional tissue trauma, such as in the brain.

For example, in an attempt to better classify stroke patients (and study stroke patients as groups), a number of standardized clinical rating scales have been developed, such as the NIH Stroke Scale (NIHSS) score. The NIHSS is a 15-item, clinical evaluation instrument used in clinical trials and practice to assess neurological outcome and degree of recovery.

Such assessment tools assign a numerical score (e.g., 0 to 42 in the case of the NIHSS) to attempt to summarize a given patient's degree of disability based on a qualitative evaluation of the patient. In general, the higher the score, the higher the deficit. Such scores are widely used as indicators of outcome for stroke.

SUMMARY

The invention is based, at least in part, on the discovery that if one uses imaging-based techniques to identify and analyze the location of tissue, e.g., in the brain, that has been damaged by some disorder, e.g., disease or trauma, and combines that information with data relating to the extent of the deficit caused by the damage, one can create a so-called "hazard atlas" of the tissue. Such a hazard atlas can be used to obtain a quantitative, imaging-based analysis of the severity of a current or future tissue disorder in patients. For example, a hazard atlas of the brain can be used to assess the prognosis of a patient who has had a stroke.

The imaging-based method applies a weight or value to each volume element (voxel, e.g., a cubic millimeter), or combination of volume elements, in the tissue based on the impact an infarction or other damage in that volume element of the tissue, e.g., the brain, would have on the prognosis of a patient. The spatial impact of an infarct or other tissue trauma is stored in the hazard atlas. The new diagnostic methods apply such a hazard atlas to patient images to compute a hazard score (or display a hazard map) for that patient.

In general, the invention features hazard atlases of a disorder (such as stroke) in a tissue (e.g., the brain; heart, or a joint) including an image of the tissue (e.g., a three-dimensional image), wherein the image has a plurality of voxels, each voxel representing a hazard value of an extent of deficit caused by damage from the disorder to that voxel of tissue at that location. In these atlases, the hazard value of each voxel can be based on any one or more of anatomical, vascular, and functional regions of tissue scored according to a specific numerical rating scale. Alternatively, the hazard value of each voxel can be based on actual patient images (e.g., from 200 patients) and recorded patient behavior and outcomes.

In certain embodiments, the tissue can be brain tissue, and the hazard value for each voxel can be determined by analyzing a set of images from a group of patients that correlates damage in a specific region of the brain with a degree of loss of function and wherein the hazard value is commensurate with the degree of loss of function.

The hazard atlas can further include a scale that correlates the values of the voxels to a code. For example, the code can be color, a series of numbers, or a gray scale. The hazard atlas can be comprised of digital data (e.g., lists of numbers and locations) and can be stored on a computer-readable medium.

In another aspect, the invention features systems for determining a hazard score for a patient having a disorder in a tissue. The systems include a device arranged to obtain or store an image of the patient's tissue, wherein the image includes a plurality of patient image voxels; a memory or computer-readable medium storing a hazard atlas of a disorder in the tissue, wherein the hazard atlas is comprised of a plurality of voxels, each voxel representing a hazard value of an extent of deficit caused by damage from the disorder to that voxel of tissue at that location; an output device; and a processor linked to the imaging device, memory, and output device. The processor is programmed to (i) obtain the image of a tissue of the patient; (ii) identify voxels of the patient image that are damaged by the disorder as damaged patient image voxels; (iii) obtain from the memory or computer-readable medium the hazard atlas of the disorder in the tissue; (iv) compute a hazard score for the patient, wherein the score is the integration of all damaged patient image voxels weighted by a hazard value corresponding to that voxel location; and (v) transmit the hazard score to the output device.

In this system, the device to obtain the image of the patient's tissue can be a magnetic resonance imaging device; the hazard atlas can be of the brain affected by stroke. The hazard atlas can include a scale that correlates the values of the voxels to a code. The damaged patient image voxels can be identified using an image segmentation method, and the image of a tissue of the patient can be comprised of a series of images to represent a three-dimensional image.

In yet another aspect, the invention features methods for determining a patient's hazard score for a disorder (such as stroke or trauma) in a tissue (e.g., the brain or a joint, such as the knee) by obtaining an image of a tissue of the patient, wherein the image comprises a plurality of patient image voxels; identifying voxels of the patient image that are damaged by the disorder as damaged patient image voxels; obtaining a hazard atlas of the disorder in the tissue; wherein the hazard atlas comprises a plurality of voxels, each voxel representing a hazard value of an extent of deficit caused by damage from the disorder to that voxel of tissue at that location; and computing a hazard score for the patient, wherein the score is the integration of all damaged patient image voxels weighted by a hazard value corresponding to that voxel location. The hazard score can be used to determine the patient's prognosis.

The methods can further include matching the patient image to a standardized set of anatomical images of that tissue to provide a standardized image, and can be used to determine a course of treatment based on the hazard score.

In other aspects, the invention includes methods for determining the efficacy of a treatment method for a patient having a tissue disorder by administering a treatment to the patient; measuring a hazard score using the new methods described herein at two or more points in time after administering the treatment; and determining the efficacy of the treatment based on the hazard scores.

The invention also includes methods of generating expert or data-driven hazard atlases by either identifying one or more of anatomical, vascular, and functional regions on a standard set of anatomical images of a tissue; assigning weighting factors to the regions according to clinically-relevant assessment methodologies; and generating an expert hazard atlas of the tissue comprising a plurality of voxels based on the weighting factors for each voxel in the atlas; or acquiring patient image data; matching patient image data to a standardized set of anatomical images; identifying regions of the patient's tissue with damage based on the image data; assigning weighting factors to the regions based on actual patient outcome data; and generating a data-driven hazard atlas of the tissue comprising a plurality of voxels based on the weighting factors for each voxel in the atlas.

In another aspect, the invention includes a computer program for determining a hazard score of a patient having a disorder in a tissue, the program residing on a computer-readable medium and having instructions for causing a processor to: (a) obtain an image of a tissue of the patient, wherein the image comprises a plurality of patient image voxels; (b) identify voxels of the patient image that are damaged by the disorder as damaged patient image voxels; (c) obtain from a memory or computer-readable medium a hazard atlas of the disorder in the tissue, wherein the hazard atlas comprises a plurality of voxels, each voxel representing a hazard value of an extent of deficit caused by damage from the disorder to that voxel of tissue at that location; (d) compute a hazard score for the patient, wherein the score is the integration of all damaged patient image voxels weighted by a hazard value corresponding to that voxel location; wherein the hazard score determines the patient's prognosis; and (e) transmit the hazard score to an output device.

The invention also includes methods of generating a combined expert- and data-driven hazard atlas by acquiring patient brain image data; matching patient brain image data to a standardized set of anatomical images; identifying regions of the patient's brain with lesions based on the image data; and assigning weighting factors to voxels comprising the hazard atlas based computational techniques (such as least squares minimization) using the acquired patient brain data, combined with expert input.

In the new methods, a hazard score can be computed by acquiring patient brain image data; matching patient brain image data to a standardized atlas; identifying regions of the patient's brain with lesions based on the image data; and computing a hazard score wherein the score is the sum of identified regions weighted by a factor for each region wherein the factor indicates an impact an infarct in that region has on a patient. For example, the weighting factor for a region can be determined by analyzing a set of images from a group of patients that correlates a lesion in the region of the brain with a degree of loss of function and wherein the weighting factor is commensurate with the degree of loss of function. Alternatively, algorithms that are more complex can be applied to analyze the patterns of tissue damage associated with various outcome scores.

The invention provides several advantages. For example, it can improve acute stroke management by better stratifying patients according to expected prognosis. Patients who are predicted by the new methods to improve substantially in the natural course of their disease could be spared risky therapeutics, whereas patients whose prognosis is poor may choose to weigh the risks associated with therapeutic options against any improvement from their natural course. The new methods can also be used in the development of novel therapies such as neuroprotective drugs or other interventions, e.g., in clinical trials, as a superior surrogate marker of clinical severity to imaging-based lesion volume alone or as a superior marker of clinical severity to clinical assessment, which may be time-consuming and carries with it a certain degree of inter-rater variability.

As in acute stroke management, the new methods can be used in the context of therapy development to stratify patients according to prognosis, as the therapeutic intervention being evaluated may be more efficacious for patients with a certain type of prognosis. The methods can also be used to more effectively evaluate the efficacy of novel therapeutic interventions by improving the statistical power of such calculations (i.e., since actual outcome with the therapeutic can be compared to potential outcome determined by the "hazard" atlases if the therapeutic were not administered, in the same patient), thus reducing sample sizes. In addition, the new "hazard" atlases will enable the generation and testing of new hypotheses to better understand, and eventually to better treat, human acute cerebral ischemia and other disorders in the brain.

In addition, while the present examples are drawn from the field of ischemic stroke, the same methodology can be applied to any pathology, inside or outside the brain, where there are imaging abnormalities and a clinical rating score. This includes other neurological illness, such a multiple sclerosis or Alzheimer's disease, where there are neuroimaging abnormalities and known rating scales. This also includes other non-neurological illness, such as cardiac disease (e.g., myocardial infarction) or joint disease (e.g., rheumatoid arthritis or osteoarthritis), where clinical scores are obtained and imaging abnormalities are present.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DETAILED DESCRIPTION

Figure 1A:
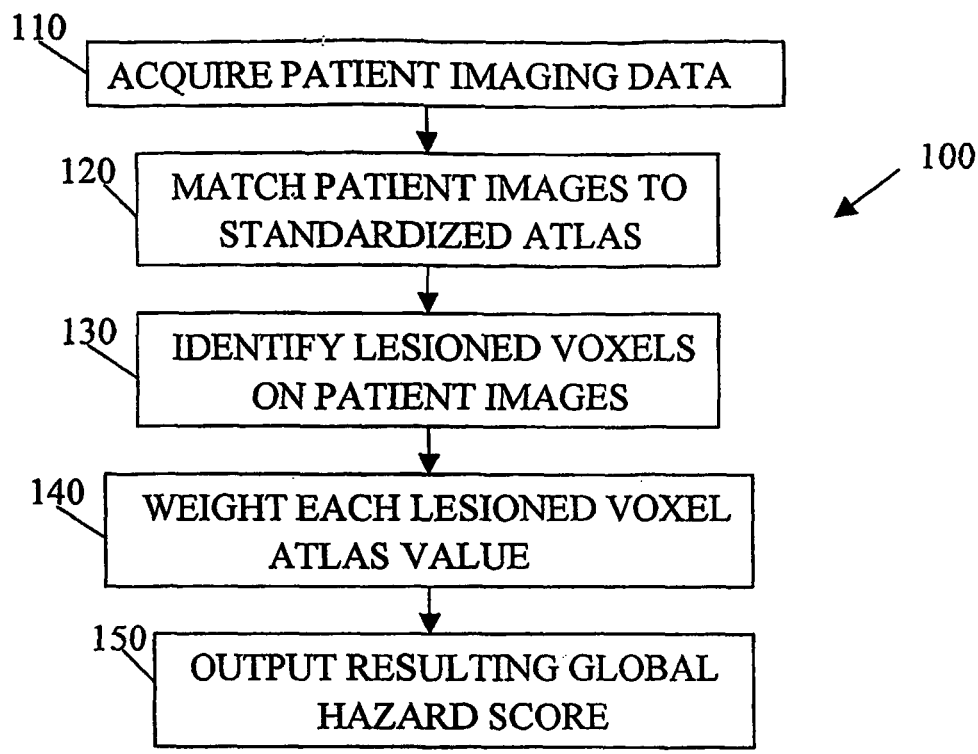
FIG. 1A is a flow chart outlining a method for determining a hazard score for a stroke patient using a weighted atlas.

Although the new methods can be applied to tissues in various locations in the body, e.g., the heart, muscles, and the brain, the new methods are described herein with respect to the brain. The new methods employ a quantitative analysis of brain images to assess the severity of a stroke or other brain disorder based on the extent and spatial position of the damaged or "at risk" tissue. First, a detailed description of the imaging method and the analysis used to assess the severity of the stroke or other disorder (measuring a "hazard score") is described. These methods assess severity in part using a weighted anatomical "hazard" atlas. Second, methods are described for producing the weighted atlas. These methods are followed by a description of methods that use the new assessment methods to determine the course of treatment for stroke patients. Next, a method is outlined that uses such assessment methods to determine the effectiveness of treatments, such as stroke therapy, by repeatedly monitoring images of patients undergoing treatments. Thereafter, examples of different ways of generating a hazard atlas, and comparisons of the effectiveness of such atlases compared to known methods of assessing patient prognosis are presented.
Measuring a Hazard Score and Producing a Weighted Hazard Atlas FIG. 1A summarizes a method 100 for measuring a hazard score (by using a hazard atlas as described in further detail below) for a patient having a brain disorder that involves lesions or death of brain tissue. Method 100 first acquires imaging data from a patient (step 110). Typically, such data is obtained using techniques such as magnetic resonance imaging (MRI) or computer tomography (CT). In embodiments using MRI, for example, images are typically acquired that highlight both anatomical features of the brain and also highlight lesions associated with stroke or other brain disorder such as Multiple Sclerosis or Alzheimer's. Suitable pulse sequences for obtaining such images are T2 weighted images (showing for example vasogenic edema formation); diffusion weighted images (showing cytotoxic edema formation); or perfusion weighted images (showing hemodynamics including regions of abnormally high or low blood flow and blood volume); T1 weighted, gradient-echo, or other structural images (showing normal and abnormal anatomy); magnetic resonance angiographic sequences (showing patency of major vessels); images after the administration of a contrast agent (showing areas of blood-brain barrier breakdown); spectroscopy (showing areas of abnormal metabolism such as increased lactate concentrations); or other types of images.

Data from other imaging modalities such as computed tomography or nuclear emission tomography could also be incorporated. In addition, the new methods can be used to diagnose any neurological disorders that cause physical or functional lesions in the brain, such as autism, schizophrenia, multiple sclerosis, Alzheimer's disease, and brain tumors.

Perfusion imaging can be obtained with the use of exogenous gadolinium-based contrast agents (see, e.g., Radiology, 210(2):519-27, 1999), or with intrinsic contrast agents (so-called arterial spin labeling). These various input images, diffusion, T2, perfusion, and potentially other input imaging data such as computed tomography, spectroscopic data, or other spatially localized information, can then be processed either singly or in a combined way (e.g., as risk maps, see Wu et al, Stroke, 32(4):933-42, 2001) to identify regions of potential abnormality.

The method next matches or co-registers (e.g., by computer) the set of patient images to a standardized set of anatomical images of the brain ("standardized atlas") (Step 120), e.g., research brain atlases (e.g., splweb.bwh.harvard.edu:8000/pages/images_movies.html) or commercial brain atlases (e.g. available on the Internet at cortechs.net/atlas) and in textbooks as listed below to obtain a set of standardized images. The standardized atlas spatially identifies the various anatomical features of a normal human brain, and the matching is done to transform all patient data to a common, stereotaxic space. Using such an atlas, the method assigns each portion or "volume element" (also known as a voxel) of the brain to an anatomical region of the atlas. These voxels are of a standard size, e.g., 1 cm³.

Next, the patient brain images are analyzed to identify the damaged voxels, e.g., those having a lesion, and segmenting the images into normal and damaged voxels (Step 130). Such image segmentation methods are widely used in neuroimaging research and can be automated or done manually (see, for example, Brain Atlas for Functional Imaging: Clinical and Research Applications, by Wieslaw L. Nowinski et al. (Thieme Medical Pub; ISBN: 0865779279; Cd-Rom edition (Feb. 15, 2001) and Co-Planar Stereotaxic Atlas of the Human Brain: 3-Dimensional Proportional System: An Approach to Cerebral Imaging, by Jean Talairach, Pierre Tournoux (Thieme Medical Pub; ISBN: 0865772932; (Jan. 15, 1988)); on the Internet, see, e.g., loni.ucla.edu/~thompson/disease atlases or mgh.harvard.edu/cma/CMA.homepage).

In some embodiments, such a determination is binary, i.e., the method determines that the tissue in a voxel is or is not lesioned, and can set the lesioned tissue to 1 and the normal tissue to 0 (or vice versa). In other embodiments, such a determination is continuous; the method determines the extent or percentage of the tissue volume element that is either infarcted or damaged or on the path to infarction. In a typical embodiment, the method analyzes T2, diffusion, and perfusion images (along with relevant clinical information such as time from onset of symptoms) to estimate the risk of infarction if no treatment is applied. The voxel-by-voxel estimate of risk of infarction might typically be calculated in a manner similar to published techniques (see, e.g., Stroke, 32(4):933-42, 2001). A coregistration transformation matrix can then be applied to the segmented lesion data set to ensure that all data sets are analyzed in a common, stereotaxic space.

Having identified anatomical regions of the images and having the spatial location of lesions (damaged voxels), the method generates an overall hazard score by the extent and location of the lesions as compared to the hazard atlas (which is different from the standardized or normal brain atlas of step 120), which indicates the deficit or "hazard" associated with having a lesion in each voxel in the brain (Step 140). The hazard atlas weights lesions in various anatomical regions differently depending on the impact such a lesion has on the type of assessment being performed. For example, in embodiments directed at motor skills, a lesion in the primary motor cortex is typically weighted heavily due to its large impact on motor skills, while a lesion in the frontal lobes may not be as heavily weighted. By summing the weights for each identified lesion over all the voxels in the image data of the patient's brain, the method produces a numerical hazard score (Step 150). The computation of the hazard score is described in further detail below and in the Examples. Alternatively, one can use the integrated image and hazard atlas to provide a hazard map of the patient's damaged voxels (in those case in which healthy voxels are set to 0).

Figure 1B:
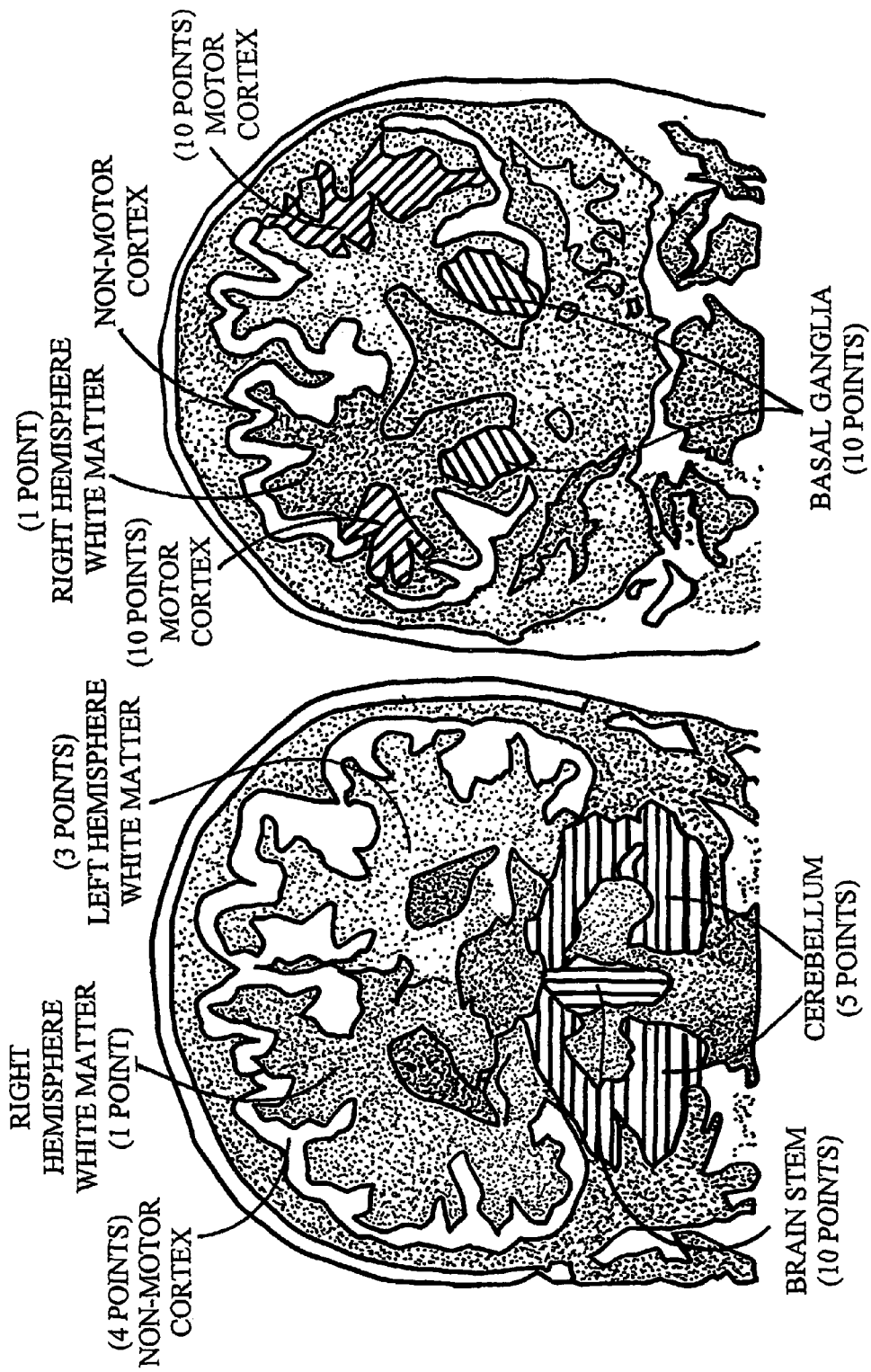
FIG. 1B is a brain atlas based on an MRI scan and provides an outcome score based on the well-known NIH stroke scale.

FIG. 1B shows a schematic of a possible brain hazard atlas based on an outcome score such as the NIH stroke scale (NIHSS) score. Coronal slices from an MRI are coded, e.g., by color, gray-scale, or numbers according to their weights. FIG. 1B uses various shadings and cross-hatching marks to indicate different regions of importance. Areas near the motor cortex (▨), basal ganglia (▧), or brainstem (▦), are weighted heavily with 10 points per voxel. Right hemisphere white matter (dark gray) has a lower score (e.g., 1 point) than left hemisphere white matter (light gray, 3 points), because language is typically located in the left hemisphere. Other areas include the cerebellum (▤), intermediate weight of 5 points; and non-motor cortex (white; 4 points).

In some embodiments, the weighted hazard atlas also includes error estimations for each of the weights. Using standard statistical techniques such as linear estimation models, the method computes statistical parameters such as confidence levels, variance, or statistical error based on the errors in the images and the errors in the atlas.

Figure 2:
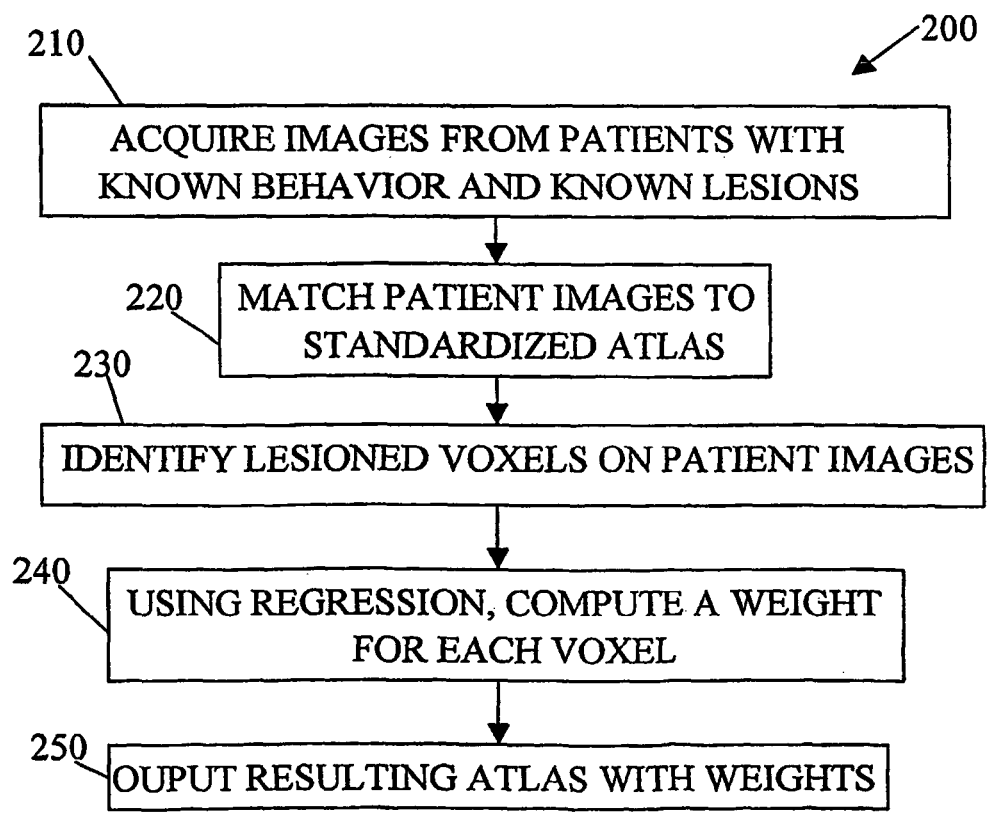
FIG. 2 is a flowchart outlining a method for determining a weighted hazard atlas.

FIG. 2 illustrates a generalized method 200 for producing a weighted hazard atlas. The method acquires brain images from patients with a stroke or other brain disorder and information on known behavior (Step 210). The method matches or co-registers the images to a standardized anatomical atlas (Step 220). As discussed above, the method assigns each voxel of the brain to an anatomical region of the atlas. The method analyses the images as described above and identifies the lesioned voxels (Step 230). The cumulative effect of the lesions in the patient causes, in part, the known behavior. The method uses regression methods and computes a weight for each voxel such that a hazard score using such weights would produce a score that is commensurate with the patient's known behavior (Step 240). Typical regression methods include linear regression models such as a Generalized Linear Model. Non-linear models can also be used. Having produced the weighted hazard atlas by regression, the method outputs the weighted hazard atlas (Step 250).

In one embodiment, a hazard atlas referred to herein as the "expert hazard atlas," is generated based on various anatomical, vascular, and functional regions outlined and scored according to NIHSS by an expert neurologist based on standard neurology textbook information (e.g., Duvernoy, The Human Brain, Surface, blood supply, and three-dimensional sectional anatomy (Heidelberg, Germany: Springer-Verlag; 1999) or Stroke Syndromes, Caplan (ed.) (New York: Cambridge University Press; 1995)), as well as the expert's clinical experience. Patient images, e.g., MR images, are obtained using standard techniques. On each image, the lesions are outlined and a binary mask is created (setting lesioned, infarcted voxels to 1 and normal, healthy voxels to 0). In addition, brain tissue that does not contribute to the NIHSS can be given a value of zero.

Data set coregistration (or matching) is performed on the MR images using registration software, such as FLIRT software (image Analysis Group, FMRIB, Oxford, UK) (see, e.g., Jenkinson et al., Med. Image Anal., 5(2):143-56 (2001) and Jenldnson et al., Neuroimage, 17(2):825-41 (2002)) to convert the anatomical images to Talairach space (Talairach et al., Co-planar Stereotaxic Atlas of the Brain (Stuttgart, Germany, Thieme, 1988). The coregistration transformation matrix for each patient is then applied to the binary lesion mask of that patient. The resulting binarized lesion data sets can have a resolution of about 1-8 $mm^3$. The expert then assigns each voxel in the expert hazard atlas a specific hazard value based on its location in the brain, and each voxel is then divided by the volume of the region in which it resides. This last step is done to account for later acquired patient data in which the actual lesion is smaller or larger than a lesion represented in the expert atlas. Thus, the expert hazard atlas accounts for differences in lesion volume.

Figure 6:
FIG. 6 is a representation of a pair of slices of an expert hazard atlas generated using known standard textbook information of deficit correlations in different anatomical, vascular, and functional regions of the brain.

FIG. 6 illustrates a pair of slices from an expert hazard atlas for the brain as affected by a stroke. The scale for the expert atlas is in units of NIHSS score, so it theoretically ranges from 0 to 42, but can be cut off at 30 if no regions with weightings above 30 are present in the atlas. The scale can be coded in color, as a gray-scale, or by numbers.

This atlas can be applied to a set of images corresponding to a new patient as follows. First, the patient's lesion on the set of patient images is outlined, binarized (e.g., 1=lesion, 0=normal) and co-registered to the standard set of anatomical images. The resulting data set is then multiplied by the expert hazard atlas and the values of the voxels in the resulting patient-specific hazard map are then summed to come up with a Hazard Score of stroke outcome:

Hazard Score prediction of
$NIHSS = \sum_{j=1}^{N2} \sum_{i=1}^{N1} NIHSS_{i,j} / volume_i \cdot infarct\_voxel_j$ where N1 is the number of outlined regions and N2 is the total number of infarct voxels. Other, more sophisticated mathematical algorithms that account for the spatial relationships between the voxels can also be used.

In another embodiment, a hazard atlas, referred to herein as a "data-driven hazard atlas," is generated based on actual patient data and actual NIHSS scores for each patient (in the case of stroke). As in the expert atlas, patient images, e.g., MR images, are obtained using standard techniques. On each image, the lesions are outlined and a binary mask is created (1=infarct, 0=no infarct). In addition, brain tissue that does not contribute to the NIHSS can be given a value of zero. The total collection of patient data sets for a large number of different patients (one set per patient) is referred to as a "training set" and is used to generate the atlas as described below. The more patient data sets are included in the training set, the more accurate and robust the data-driven hazard atlas will be.

Patient data set coregistration is again performed on all of the MR images in the training set using registration software, such as FLIRT software. The result is used to create a 3D atlas of the brain of approximately 1-8 mm$^3$ resolution, where each voxel represents the likelihood of an infarct in that area contributing to a given outcome score. This is done by multiplying each damaged voxel in a given input binary patient data set by a coefficient corresponding to the NIH Stroke Scale (NIHSS) score assigned to that actual patient, divided by the number of damaged, lesioned voxels. Thus, the location of a single voxel associated with a high NIHSS score would get proportionately greater weight than a large lesion (covering many voxels) that has a low NIHSS score. This process is repeated for each of patient data sets. Once the complete training set is analyzed and input into the system, the resulting atlas is normalized to assign the highest value voxel in the atlas a value of 1.0.

In this data-driven atlas, each voxel in the atlas represents the mean NIHSS score of all voxels (divided by the total number of voxels) from the actual patient data sets for that specific location in the brain. Thus, while data from 45 patients provides a useful data-driven hazard atlas (as in Example 3 below), data from 200, 300, 500, 1000, or even 2000 or more patients will provide a more robust and accurate atlas. This data-driven atlas is applied to new patient data in the same way as the expert atlas.

Figure 10:
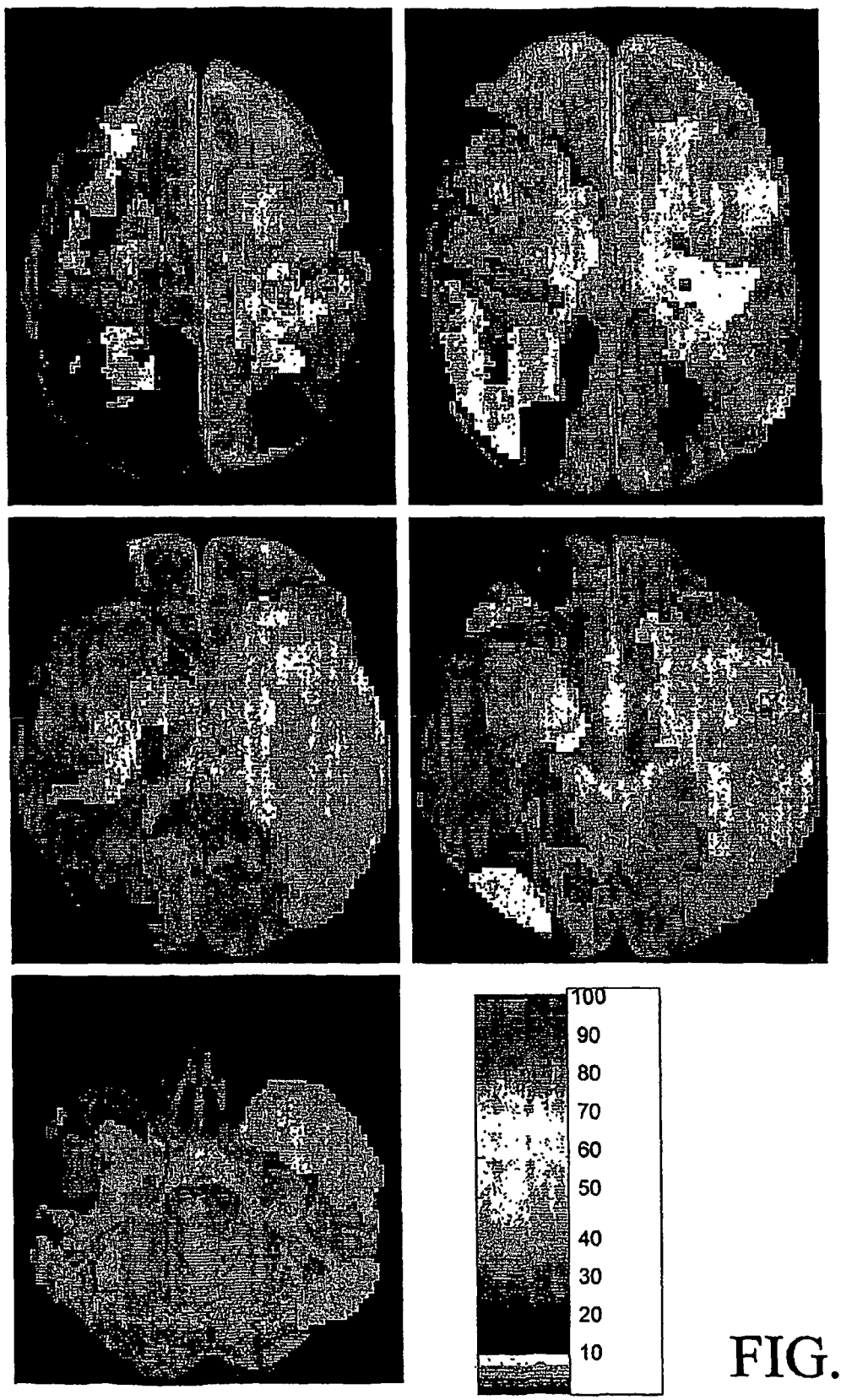
FIG. 10 is a representation of a series of slices of a data-driven hazard atlas generated using actual patient data to develop deficit correlations for different voxels of the brain.

FIG. 10 illustrates a series of slices from a data-driven hazard atlas of the brain as affected by a stroke. The scale for the data-driven atlas is in arbitrary units (scaling factors have been incorporated), and varies from 10 to 100, with 10 being low and 100 being high, and it is linear. The scale can be in color (e.g., a red-blue color scale) or displayed as a gray-scale anatomical images.

More sophisticated analytic embodiments are also possible in generating the data-driven hazard atlas. For example, the lesions may not be rated as 0 for absent or 1 for present, but on a continuum from 0 to 1 depending on severity or probability. Furthermore, the score derived for each voxel need not be a simple division process, but can involve a more complex weighting of input parameters. Another embodiment combines the input from the expert with input from the data-driven approach to generate an atlas from both the expert and data-driven results.

Some embodiments form weighted hazard atlases that are directed at various behaviors and skills. For example, certain embodiments develop a weighted atlas for language or cognition skills. Other embodiments develop a weighted atlas for motor skills. Furthermore, in some embodiments, a weighted atlas is developed directed at the various phases of treatment such as hyperacute, acute, and chronic phases. In other embodiments, the regression methods described include statistical methods that predict the confidence levels, variances, or statistical errors associated with the weights.

In certain embodiments, methods 100 and 200 are utilized simultaneously. For example, for each set of images that are acquired in embodiments of method 100, the actual outcome of the patient's condition can be retrospectively assessed. Using the combined data of images and final outcome, such data is used as an input to method 200. In this way, method 200 refines the weighted hazard atlas. In such combined embodiments, method 100 can be used to augment the data set that is used in method 200 to define the atlas. For example, in some embodiments, clinical centers that use method 100 record the patient images and the patient conditions or outcomes. These are sent to a central database automatically. For example, computer programs can automatically send appropriately anonymized images and conditions for every patient examined via the World Wide Web to a central database for patients giving consent for such collection. Such a central database uses the incoming images and conditions as input to method 200. In this way, an ever-growing data set further refines the data-driven weighted hazard atlas. Furthermore, on some periodic basis, the central database may then upgrade the weighted atlas being used by each of the clinical centers. One advantage of the data-driven hazard atlas is that it tends to average out the discrepancies that can be caused by different subjective NIHSS scores recorded by different doctors or other healthcare practitioners for similar patients.

Determining Treatment and Prognosis

Figure 3A:
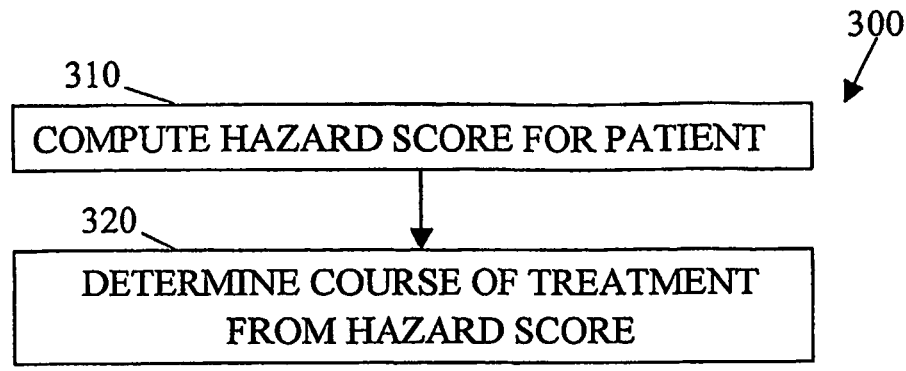
FIG. 3A is a flowchart outlining a method for determining the course of treatment for a stroke patient.
Figure 3B:
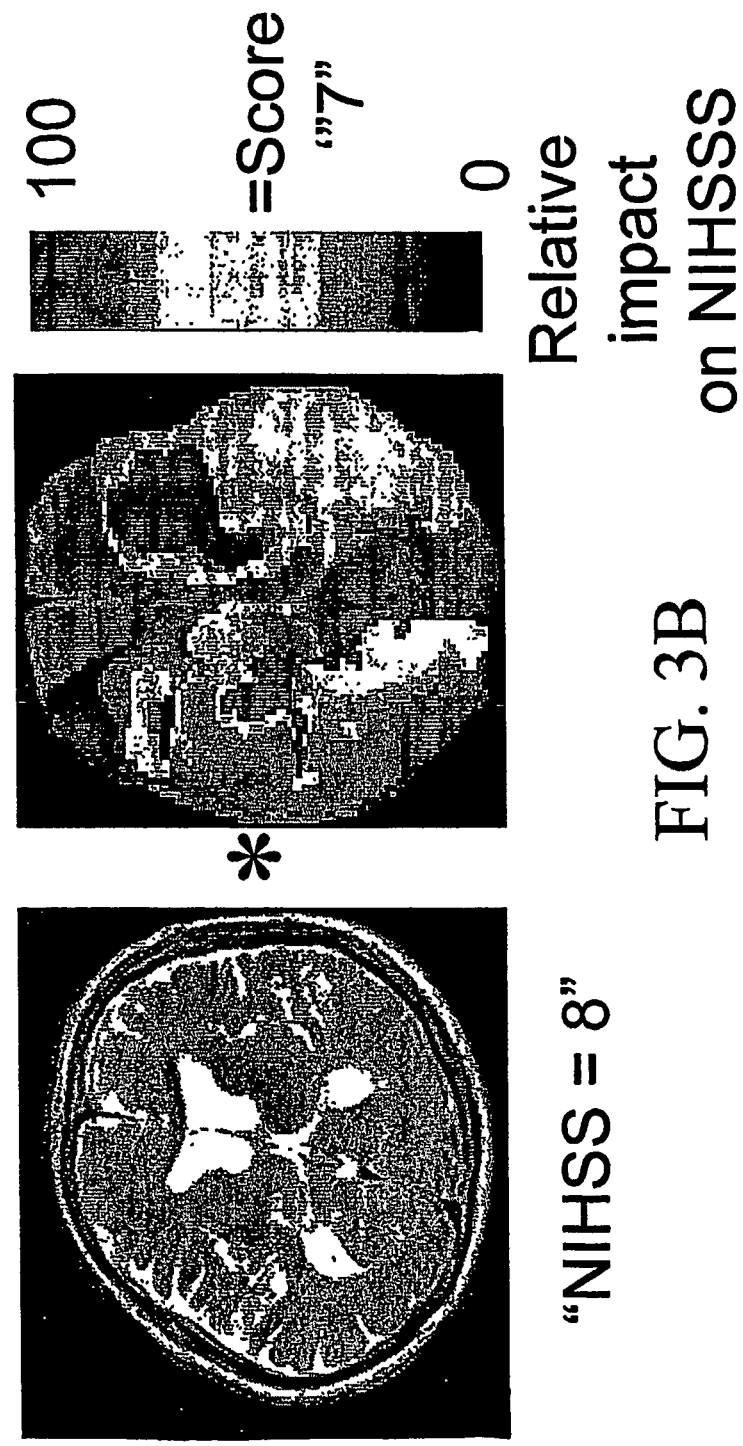
FIG. 3B is a representation of a method of generating a hazard score by combining patient images with a hazard atlas to obtain a numerical hazard score.

Referring to FIG. 3A, a method 300 for determining the course of treatment for a stroke patient is outlined. The method computes the hazard score for a patient (Step 310), as described herein. Using the hazard score, an appropriate course of treatment is determined (Step 320). In general, the method of computing a hazard score is illustrated in FIG. 3B, which shows that the patient data (DWI, T2, CT, etc.) is multiplied by the hazard atlas (and summed; e.g., integrated) to generate a numerical hazard score.

Various embodiments of method 300 assess the severity of a stroke on varying levels. In some embodiments, the hazard score is directed at assessing the patient's prognosis towards the activities of daily living. The quantitative imaging-based score produced by such an embodiment of method 300 is similar to scores such as the NIHSS score. In other embodiments, the hazard score of method 300 focuses on the language or cognition prognosis of the patient. In yet other embodiments, the hazard score of method 300 correlates with the motor skills of the patient. A user (such as a neurologist) can then use any or all of these variants to better characterize the impact of an infarct. In yet other embodiments, the output hazard score can be used as the basis for an automated treatment.

Method 300 can be used in a variety of phases of treating patients, e.g., stroke patients. For example, the hyperacute, acute, and chronic phases of treatment employ method 300 in slightly differing capacities. In the hyperacute phase, treatment choices are made. Decisions about whether or not to administer risk-bearing therapies such as thrombolytics often entail weighing what tissue is at risk. Method 300 quantifies the effect of infarction in a specific area at risk. If the tissue at risk could have a large impact on outcome, then greater risks might be undertaken to salvage such tissue. However, if the tissue at risk has only minor impact, or, if recovery from lesions in that area is known to be common, then it may be prudent to minimize the risk of a catastrophic outcome. In the acute setting, method 300 is used to determine near-term prognosis; e.g., whether or not the patient is doing better or worse than predicted by the stroke as visualized by MRI or CT. For example, the method can be used to determine whether or not a particular course of rehabilitation therapy is warranted. In the chronic setting, the method is used to further confirm the patient's progress and whether or not the expected outcome is being met.

Furthermore, risk maps that quantify the imaging correlate to the ischemic penumbra (in stroke)(see, e.g., Wu et al, Stroke, 32:933, 2001) could be linked by the new hazard atlases to provide additional information to the doctor to decide the potential clinical impact of treating or not treating a disorder. This could allow the generation of prospective Hazard Scores, thus allowing clinicians to assess quantitatively the impact of treatment decisions. The use of "risk maps" is described in detail in WO 01/56466. A risk map takes input data such as MR images from a patient and provide a prediction as to which voxels of tissue will recover and which will die as a result of damage caused by a specific disorder at the point in time when the patient images were made. For example, not all tissue affected by ischemia will die, and some tissue not directly affected, but adjacent to affected tissue may die. Risk maps provide a percentage of risk of a negative outcome for each voxel or region of the tissue, such as the brain.

Figure 3C:
FIG. 3C is a representation of a method of combining a risk map with a hazard atlas to highlight possible salvageable tissue.
Figure 3C:
Figure 3C:
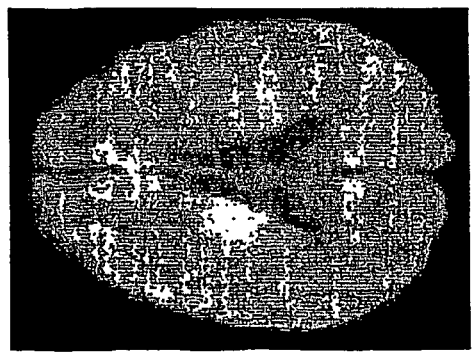
Figure 3C:

In particular, as shown in FIG. 3C, patient data is combined with (e.g., multiplied by) a risk map, e.g., as described in WO 01/56466, and the resulting combined image is multiplied by a hazard atlas to generate a "risk/reward" map or indicates the spatial impact of stroke therapy on possible outcome. Thus, for example, a doctor can focus on treating tissue that has the greatest potential to recover.

For diseases other than stroke, the appropriate intervention could be made based on the outcome of the hazard calculation. For example, if an MRI of a patient's knee generates a pattern of lesions that a hazard analysis indicates has high risk of future deterioration from rheumatoid arthritis, more aggressive anti-inflammatory treatment can be started.

Determining Efficiency of Treatment

Figure 4:
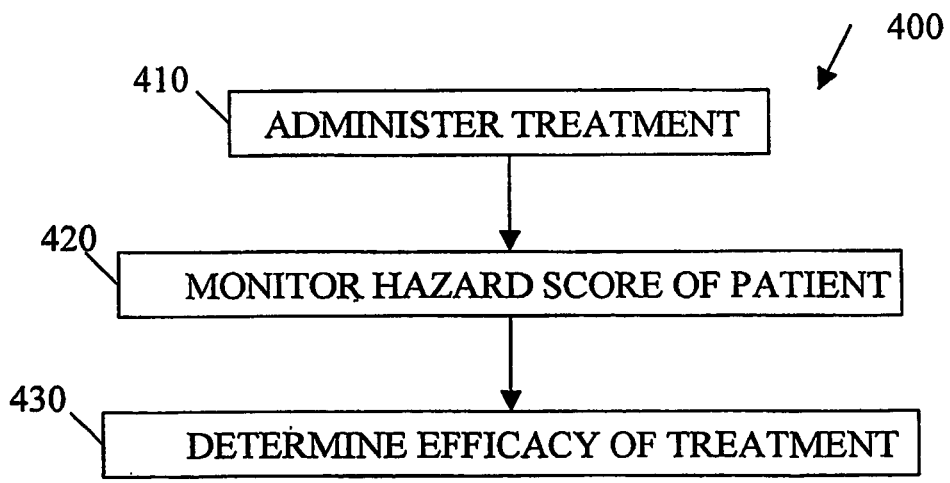
FIG. 4 is a flowchart outlining a method for determining the effectiveness of a treatment for stroke patients.

FIG. 4 summarizes a method for determining the efficacy of a treatment, e.g., for stroke. The method 400 involves administering a treatment to one stroke patient or a group of stroke patients (Step 410). During this period, the hazard score can be repeatedly measured for each patient (Step 420), using the methods described herein. The method 400 determines the efficacy of the treatment based on the trends and statistical analysis of the recorded hazard scores. Similar to the discussion of method 300 above, embodiments of method 400 monitor treatments directed towards hyperacute, acute, or chronic treatments. In some embodiments, the method determines efficacy using multiple hazard scores.

Implementation

In some embodiments, the steps described above are implemented in computer programs using standard programming techniques. Such programs are designed to execute on programmable computers each including an electronic processor, a data storage system (including memory and/or storage elements), at least one input device, and least one output device, such as a display or printer. For example, the programs, or a programmed computer, can be used in an MRI scanner. In some embodiments, the program code is applied to control the acquisition of the MRI data using a pulse sequence stored in the software. In some embodiments, the code is applied to the acquired data.(e.g., MRI data from a spectrometer), to perform the functions described herein, and to generate output information (e.g. treatment determinations, hazard scores, weighted atlases), which is applied to one or more output devices.

Each such computer program can be implemented in a high-level procedural or object-oriented programming language, or an assembly or machine language. Furthermore, the language can be a compiled or interpreted language. Each such computer program can be stored on a computer readable storage medium (e.g., CD ROM or magnetic diskette) that when read by a computer can cause the processor in the computer to perform the analysis described herein.

In particular, the hazard atlases are data sets (lists of numbers and locations) that can be in the form of computer files, e.g., stored on computer-readable storage media such as CDs, DVDs, magnetic disks, or in a computer or other system's hard drive.

EXAMPLES

The following examples describe different methods of generating and testing hazard atlases, and are not meant to be limiting.

Example 1

Generating and Using an Expert Hazard Atlas

Patients were included in this study if they had diffusion- or T2-weighted images and an NIHSS score recorded a minimum of 5 days after the onset of acute stroke symptoms. The NIHSS is a scale based on a 15-item questionnaire that scores the clinical deficit from 0 to 42 points, with a higher score corresponding to a higher deficit. The scale heavily weights motor functions, whereas level of consciousness and sensory and cortical functions are less weighted. In addition, some brain functions (or dysfunctions) do not contribute at all to the overall score. These include memory, neuropsychiatric symptoms such as compulsive behavior that are associated with the anterior frontal lobe lesions, and lower brain stem functions such as swallowing.

Data from 1446 patients obtained at the Massachusetts General Hospital (Boston, Mass., USA) between 1999 and 2003 and from 45 patients enrolled in a study at Kuopio University Hospital (Kuopio, Finland) was retrospectively reviewed. 62 patients were found to meet the inclusion criteria. Of these, 3 were excluded because of noisy data, 2 were excluded because of hemorrhage, and 2 were excluded because they had had surgery. 1 patient was excluded because of a very high NIHSS score (i.e., >30), 2 because of very large infarcts (i.e., >300 $cm^3$) that caused anatomical distortions such as midline shift, and 5 due to very small infarcts (i.e., <1 $cm^3$). The total number of patients included in the study after these exclusions was 47 with NIHSS scores ranging from 0 to 24 and infarct volumes ranging from 1.4 to 281.2 $cm^3$. Among these, 30 had right-sided infarcts, 16 had left-sided infarcts and 1 had a bilateral (cerebellar) infarct. The mean time to MRI was 9.4 days, the mean time since onset that the NIHSS score was recorded was 9.1 days, and the mean time elapsed between the MRI and NIHSS score measurement was 1.5 days.

Imaging was performed on a 1.5 T General Electric or a 1.5 T Siemens system. T2-weighted images taken at the first site, Massachusetts General Hospital, were measured using a fast spin echo sequence. 25 axial slices were acquired using TR/TE=6267/110 ms, field of view (FOV)=22 cm, matrix=256×320, and a 5 mm slice thickness with a 1 mm gap. Diffusion-weighted images were measured using a single shot echo planar sequence in 6 directions using two b values: 0 and 1000 s/$mm^2$. Imaging parameters were similar to those pertaining to the T2 sequence, except 23 axial slices were acquired using TR/TE=7500/118 ms, FOV=22×20 cm, and matrix=128.

Diffusion-weighted images taken at the second site, Kuopio University Hospital, were measured using an echo planar sequence in 3 orthogonal directions using a b value of 1000 s/$mm^2$. 19 axial slices were acquired using TR/TE=4000/103 ms, FOV=26 cm, matrix=96×128 (interpolated to 256×256), and a 5 mm slice thickness with a 1.5 mm gap. T2-weighted images were measured in a similar fashion using a b value of 0.

On each image, the lesion was outlined and a binary mask created (1=infarct, 0=no infarct). Data set coregistration was performed on the MR images using FLIRT software (Image Analysis Group, FMRIB, Oxford, UK) (Jenkinson, supra), converting the anatomical images to Talairach space (Talairach, supra). The coregistration transformation matrix for each patient was then applied to the binary lesion mask of that patient. The resulting binarized lesion data sets had a resolution of 2 mm³.

The effect of lesion location was quantified based on expected stroke outcome in which various anatomical, vascular, and functional regions were outlined and scored according to NIHSS by an expert neurologist based on standard neurology textbook information (Duvernoy, supra, Stroke Syndromes, supra). Each voxel in the expert hazard atlas was then divided by the volume of the region it resided in. The resulting set of voxels was then multiplied by each infarct and then summed to come up with a Hazard Score of stroke outcome:

$$\text{Hazard Score prediction of NIHSS} = \sum_{j=1}^{N2} \sum_{i=1}^{N1} \text{NIHSS}_{i,j} / \text{volume}_i \cdot \text{infarct\_voxel}_j \quad (1)$$

where N1 is the number of outlined regions and N2 is the total number of infarct voxels. Not all brain tissue was outlined and scored in the expert hazard atlas; brain tissue that was deemed to not contribute to the NIHSS was given a value of zero.

Example 2

Testing an Expert Hazard Atlas

To gauge the improvement in the prediction of NIHSS by including lesion location (rather looking just at lesion volume), linear regression was used to develop a prediction of NIHSS using lesion volume alone:

$$\text{Volume Score prediction of NIHSS} = b_0 + b_1 \cdot \text{volume} \quad (2)$$

The terms $b_0$ and $b_1$ were retained if they were found to contribute significantly to the fit. A leave-one-out cross-validation method was used in which the 'Volume Score' computed for a given patient was based on an atlas developed from the remaining 46 patients.

Correlation analysis was then performed for Volume Score vs. NIHSS and Hazard Score vs. NIHSS by computing Pearson's correlation coefficient and comparing the significance of the difference between the two correlation coefficients. The performance of the two predictive models was additionally compared by calculating how often the Hazard Score predictions were closer to the measured NIHSS scores than the Volume Score predictions and then using the exact binomial test to determine the probability of this occurrence.

Figure 5A:
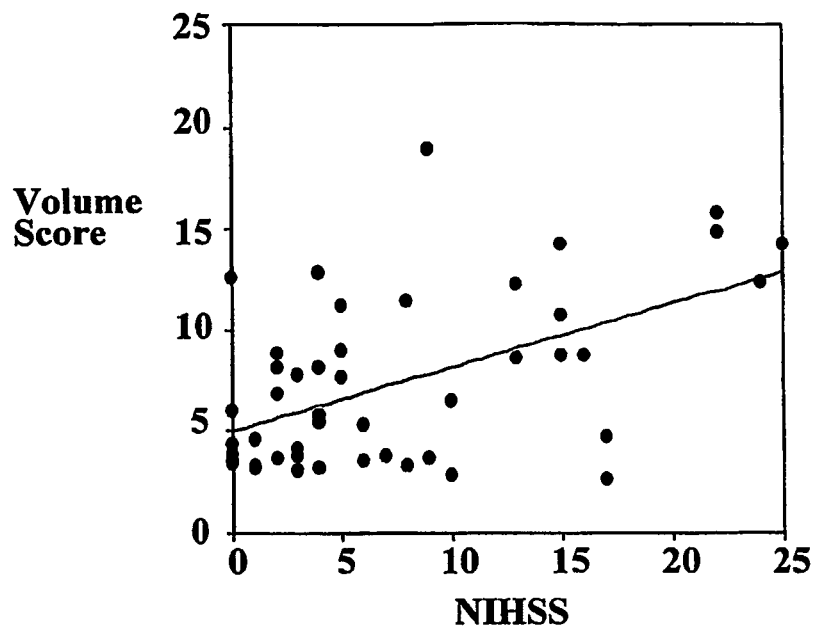
FIGS. 5A and 5B are a pair of graphs comparing the correlation coefficients of volume score v. NIHSS (5A) and hazard score v. NIHSS (5B) based on a hazard atlas generated using standard textbook information of deficit correlations in different anatomical, vascular, and functional regions of the brain.
Figure 5B:
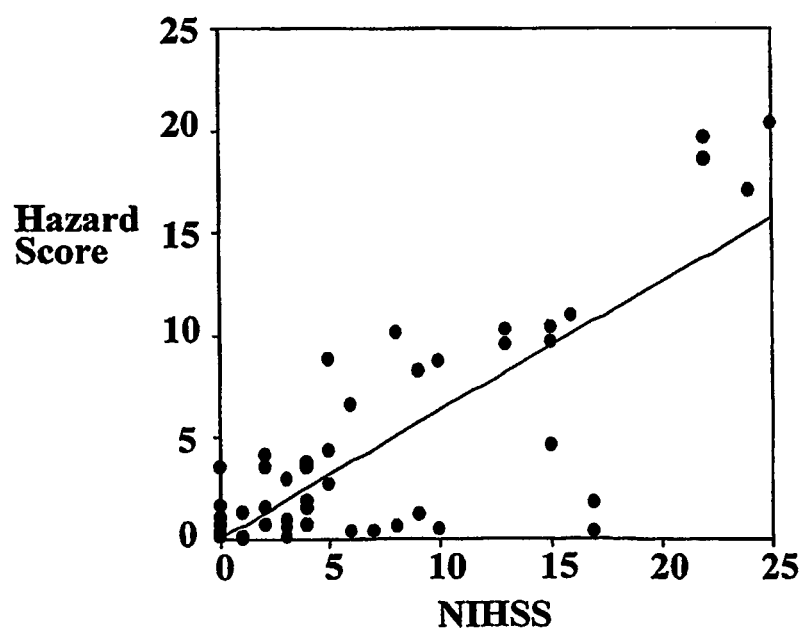

The correlation between Volume Scores and NIHSS scores was $r=0.53$ ($p<0.01$). Volume Scores use volume alone to predict NIHSS scores according to equation (2) above. Both terms $b_0$ and $b_1$ were retained in the fit. The correlation between Hazard Scores and NIHSS scores was $r=0.79$ ($p<0.01$). Thus, Hazard Scores, which incorporate lesion location as well as volume, better predicted NIHSS scores than Volume Scores ($p=0.021$ comparing the two correlation coefficients). FIGS. 5A and 5B show the two correlation plots (5A represents the Volume Score, and 5B represent the Hazard Score). FIG. 6 shows two representative slices from the expert hazard atlas.

Hazard Scores better predicted NIHSS scores than Volume Scores in 31 out of 47 cases. The probability of this occurring by chance is low: 2.0% (assuming that each set of predictions is equally likely to be closer to the measured NIHSS scores).

Figure 7A:
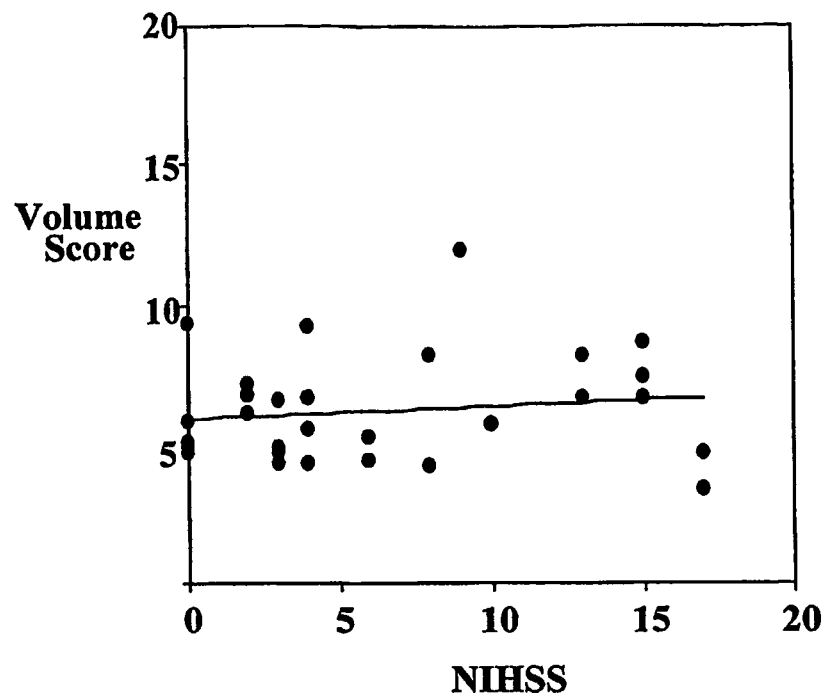
FIGS. 7A and 7B are a pair of graphs comparing the correlation coefficients of volume score v. NIHSS (7A) and hazard score v. NIHSS (7B), looking only at right hemisphere infarcts.
Figure 7B:
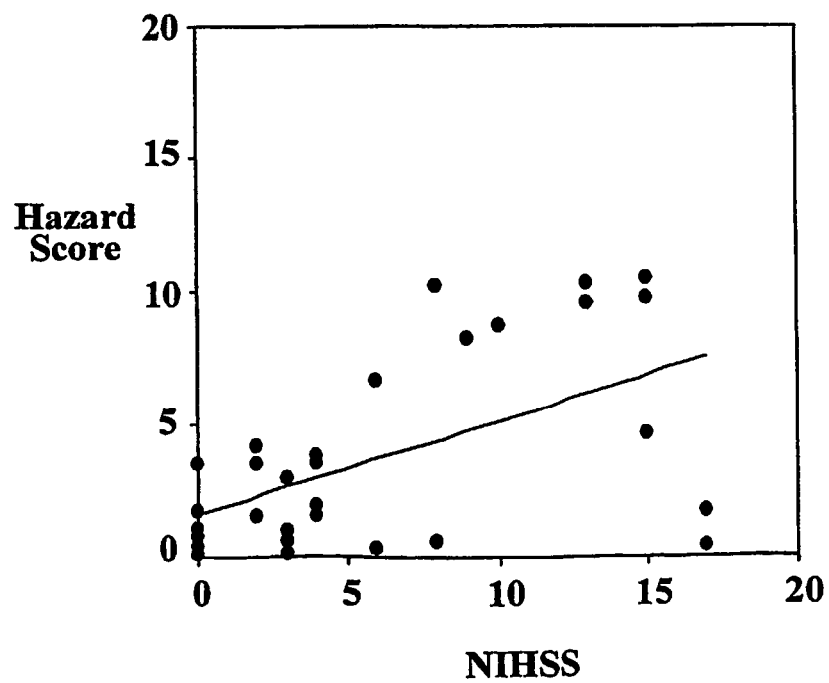

The data was then separated into right- and left-sided infarcts and analyzed separately. 30 out of the 47 patients had right-sided infarcts (16 had left-sided infarcts and 1 had a bilateral cerebellar infarct). The correlation between Volume Scores and NIHSS scores was $r=0.14$ ($p<0.01$) and between Hazard Scores and NIHSS scores was $r=0.55$ ($p<0.01$). FIGS. 7A and 7B show the two correlation plots. The improvement in prediction of NIHSS scores provided by the "hazard" atlas over volume alone was nearly significant ($p=0.078$, comparing correlation coefficients for the Hazard Score predictions of NIHSS scores compared to the Volume Score predictions). In addition, Hazard Scores better predicted NIHSS scores than Volume Scores in 19 out of 30 cases. The probability of this occurring by chance is relatively low: 10.0%. The 11 out of 30 cases that were better predicted by volume corresponded to significantly smaller infarct volumes than the 19 cases that were better predicted by the 'hazard' atlas methodology ($p=0.022$). There was no difference between the two groups in terms of measured NIHSS scores.

Figure 8A:
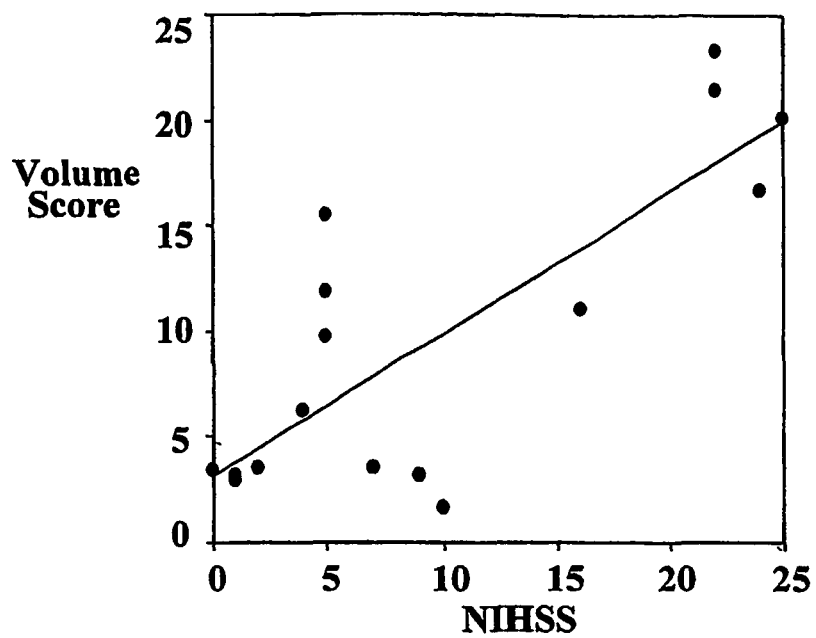
FIGS. 8A and 8B are a pair of graphs comparing the correlation coefficients of volume score v. NIHSS (8A) and hazard score v. NIHSS (8B), looking only at left hemisphere infarcts.
Figure 8B:
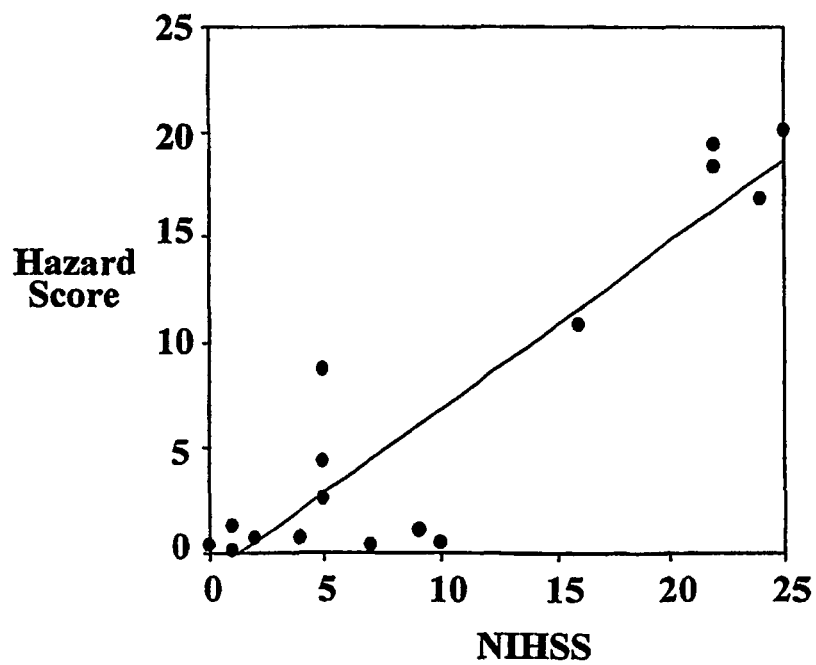

16 out of the 47 patients had left-sided infarcts. The correlation between Volume Scores and NIHSS scores was $r=0.80$ ($p<0.01$) and between Hazard Scores and NIHSS was $r=0.92$ ($p<0.01$). FIGS. 8A and 8B show the two correlation plots. The difference between the two correlation coefficients in this small subset of cases was not significant ($p=0.218$). Hazard Scores better predicted NIHSS scores than Volume Scores in 9 out of 16 cases. The probability of this occurring by chance is moderate: 40.2%. There was no significant difference between 7 out of 16 the cases that were better predicted by volume and 9 cases that were better predicted by the "hazard" atlas methodology in terms of infarct volumes or measured NIHSS scores.

These results indicate that the inclusion of location in a volume-based assessment of stroke severity significantly improves the correlation between imaging and outcome. In addition, the correlation coefficient obtained when location was included ($r=0.79$) is high enough to be of predictive value.

Example 3

Generating a Data-Driven Hazard Atlas

The criteria for patient selection were generally the same as in Example 1, with the additional criterion that the lesion corresponding to each patient had to overlap with the lesions corresponding to the remainder of the patients by 50% or more. Due to this criterion, an additional 2 patients were excluded, leaving a total of 45 patients.

Data was prepared as in Example 1 with respect to outlining lesions, created binary masks, and co-registration. On each image, the lesion was outlined and a binary mask created (1=infarct, 0=no infarct). Data set co-registration was performed using FLIRT software (Image Analysis Group, FMRIB, Oxford, UK). The result was then used to create a 3D atlas of the brain of 8 mm³ resolution, where each voxel represented the likelihood of an infarct in that area contributing to a given outcome score. This was done by using least squares regression in which the patient data sets and their corresponding NIHSS scores were treated as a system of linear equations represented in the following equation with matrices:

$$A \cdot x = b \quad (3)$$

where A is a matrix consisting of patient data (in which each row corresponds to a vector representation of a different binarized, co-registered patient data set), x is the vector representation of the hazard atlas, and b is a vector containing the NIHSS scores that correspond, row-by-row, to the patients in matrix A.

A solution for x was obtained using least squares minimization. A 3D matrix representation of x (i.e., the data-driven atlas) was obtained by reshaping the vector using the appropriate dimensions. A leave-one-out cross-validation (jack-knifing) method was used in which the data-driven atlas applied to a given patient was based on data from the remaining 44 patients. Thus, for 45 patients, 45 atlases were created, each based on data from 44 patients. One such atlas is shown in FIG. 10.

A Hazard Score was obtained for each patient by multiplying the data-driven atlas by that patient's binarized, co-registered data set, and computing the sum across voxels.

Example 4

Testing a Data-Driven Hazard Atlas

The data-driven hazard atlas was tested in an identical manner as the expert hazard atlas, as described in Example 2.

Figure 9A:
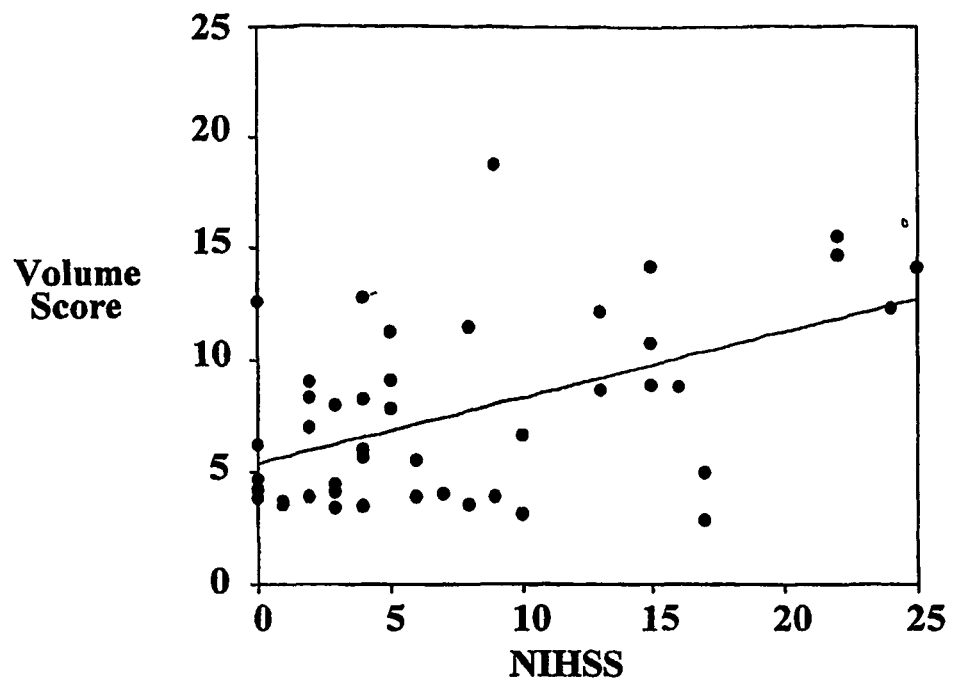
FIGS. 9A and 9B are a pair of graphs comparing the correlation coefficients of volume score v. NIHSS (9A) and hazard score v. NIHSS (9B) based on a hazard atlas generated using actual patient data to develop deficit correlations for different voxels of the brain.
Figure 9B:
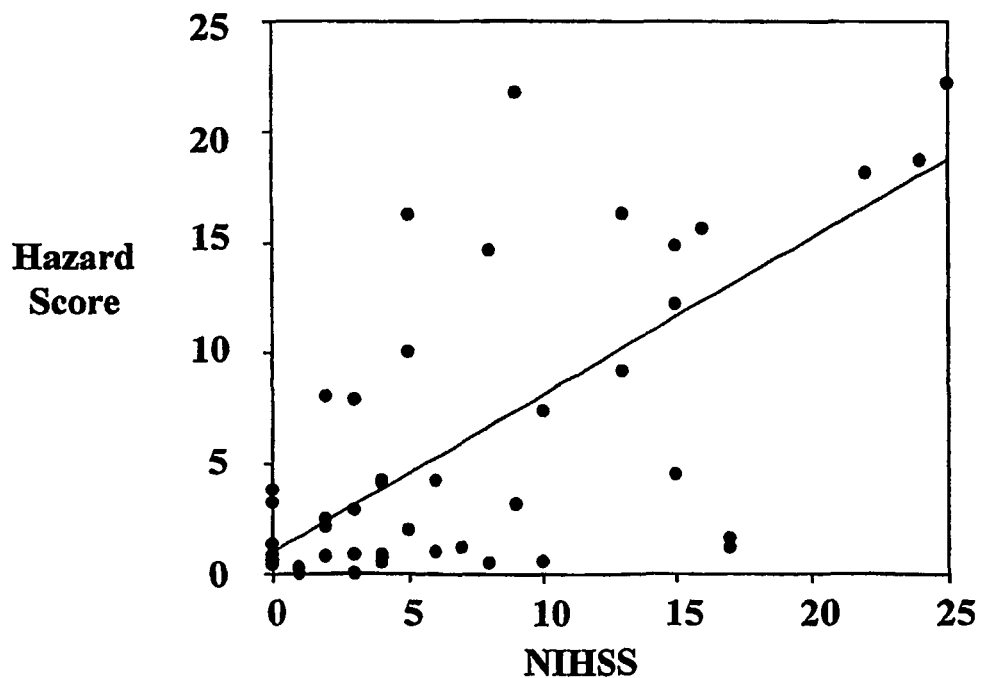

The correlation between Volume Scores and NIHSS scores was r=0.51 (p<0.01). Volume Scores use volume alone to predict NIHSS scores according to equation (2) in Example 3. Both terms $b_0$ and $b_1$ were retained in the fit. The correlation between Hazard Scores and NIHSS scores was r=0.69 (p<0.01). Thus, Hazard Scores, which incorporate lesion location as well as volume, tending to better predict NIHSS scores compared to Volume Scores (p=0.190 comparing the two correlation coefficients). However, in the present experiment, this improvement did not reach statistical significance for the sample size used here. FIGS. 9A and 9B show the two correlation plots (9A represents the Volume Score, and 9B represent the Hazard Score). FIG. 10 shows representative slices from the data-driven hazard atlas.

Hazard Scores better predicted NIHSS scores than Volume Scores in 26 out of 45 cases. The probability of this occurring by chance is moderate: 18.6% (assuming that each set of predictions is equally likely to be closer to the measured NIHSS scores). Based on these results, a data-driven hazard atlas based on patient data from 200 or more patients will provide a robust atlas.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A system for determining a hazard score for a patient having a disorder in a patient tissue, comprising a device arranged to obtain or store an image of the patient's tissue, wherein the image comprises a plurality of patient image voxels; a memory or computer-readable medium storing a non-patient specific hazard atlas of a disorder in a tissue, wherein the hazard atlas comprises a plurality of voxels, each voxel representing a hazard value of an extent of deficit caused by damage from the disorder to that voxel of the tissue at that location, such that the hazard value contains location specific information about the impact that the voxel's death would have on behavior; an output device; and a processor linked to the imaging device, memory, and output device, wherein the processor is programmed to (i) obtain the image of the patient's tissue; (ii) identify voxels of the patient image that are damaged by the disorder as damaged patient image voxels; (iii) obtain from the memory or computer-readable medium the hazard atlas of the disorder in the tissue; (iv) compute a hazard score for the patient, wherein the score is the integration of all damaged patient image voxels weighted by the hazard value corresponding to that voxel location; and (v) transmit the hazard score to the output device.

2. The system of claim 1, wherein the device to obtain the image of the patient's tissue is a magnetic resonance imaging device.

3. The system of claim 1, wherein the hazard atlas is an atlas of the brain affected by stroke.

4. The system of claim 1, wherein the hazard atlas comprises a scale that correlates the values of the voxels to a code.

5. The system of claim 1, wherein the hazard score is computed using the formula:

$$\text{Hazard Score} = \sum_{j=1}^{N2} \sum_{i=1}^{N1} \text{National Institute of Health Stroke Scale}_{i,j}/\text{volume}_i \cdot \text{infarct\_voxel}_j$$

where N1 is the number of outlined regions and N2 is the total number of infarct voxels.

6. The system of claim 1, wherein damaged patient image voxels are identified using an image segmentation method.

7. The system of claim 1, wherein the image of a tissue of the patient comprises a series of images to represent a three-dimensional image.

8. The system of claim 1, wherein the hazard value of each voxel is based on any one or more of anatomical, vascular, and functional regions of tissue scored according to a specific numerical rating scale.

9. The system of claim 1, wherein the hazard value of each voxel is based on patient images and recorded patient behavior and outcomes.

10. The system of claim 1, wherein the tissue is brain, and the hazard value for each voxel is determined by analyzing a set of images from a group of patients that correlates damage in a specific region of the brain with a degree of loss of function and wherein the hazard value is commensurate with the degree of loss of function.

11. The system of claim 1, further comprising a scale that correlates the values of the voxels to a code.

12. The hazard atlas of claim 11, wherein the code is color.

13. The system of claim 11, wherein the code is a series of numbers.

14. The hazard atlas of claim 11, wherein the code is a gray scale.

15. The system of claim 1, wherein the image of the tissue is a three-dimensional image.

16. The system of claim 1, wherein the tissue is brain.

17. A system for producing a hazard score, the system comprising a device arranged to obtain or store an image of a patient's tissue, wherein the image comprises a plurality of patient image voxels; a memory or computer-readable medium storing a non-patient specific hazard atlas of a disorder in a tissue, wherein the hazard atlas comprises a plurality of voxels, each voxel representing a hazard value of an extent of deficit caused by damage from the disorder to that voxel of the tissue at a specific location, such that the hazard value contains location specific information about the impact that the voxel's death would have on behavior; an output device; and a processor linked to the imaging device, memory, and output device, wherein the processor is programmed to (i) obtain the image of the patient's tissue; (ii) identify voxels of the patient image that are damaged by the disorder as damaged patient image voxels; (iii) obtain from the memory or computer-readable medium the hazard atlas of the disorder; (iv) compute a hazard score for the patient, wherein the score is the integration of all damaged patient image voxels weighted by the hazard value from the hazard atlas corresponding to that voxel location; and (v) transmit the hazard score to the output device.

* * * * *